US008805540B2

(12) United States Patent  
Lloyd et al.

(10) Patent No.: US 8,805,540 B2
(45) Date of Patent: Aug. 12, 2014

(54) MRI COMPATIBLE CABLE

(71) Applicant: Imricor Medical Systems, Inc., Burnsville, MN (US)

(72) Inventors: Thomas W. Lloyd, Eagan, MN (US); Steven R. Wedan, Savage, MN (US); Gregg S. Stenzel, Victoria, MN (US)

(73) Assignee: Imricor Medical Systems, Inc., Burnsville, MN (US)

( * ) Notice: Subject to any disclaimer, the term of this patent is extended or adjusted under 35 U.S.C. 154(b) by 0 days.

(21) Appl. No.: 13/833,533

(22) Filed: Mar. 15, 2013

(65) Prior Publication Data

US 2013/0199839 A1    Aug. 8, 2013

Related U.S. Application Data

(63) Continuation-in-part of application No. 12/743,954, filed as application No. PCT/US2010/026232 on Mar. 4, 2010, now Pat. No. 8,588,934.

(60) Provisional application No. 61/660,085, filed on Jun. 15, 2012, provisional application No. 61/157,482, filed on Mar. 4, 2009.

(51) Int. Cl.
    *A61N 1/04* (2006.01)

(52) U.S. Cl.
    USPC .......... 607/116; 607/117; 607/118; 607/119; 607/63

(58) Field of Classification Search
    CPC .................................. A61N 2001/086
    USPC .......................... 607/116–119, 63
    See application file for complete search history.

(56) References Cited

U.S. PATENT DOCUMENTS

| 3,380,004 | A | 4/1968 | Hansen |
| 5,039,964 | A | 8/1991 | Ikeda |
| 5,209,233 | A | 5/1993 | Holland et al. |
| 5,217,010 | A | 6/1993 | Tsitlik et al. |
| 5,304,219 | A | 4/1994 | Chernoff et al. |

(Continued)

FOREIGN PATENT DOCUMENTS

WO    WO 2007/047966 A2    4/2007

OTHER PUBLICATIONS

Third-Party Submission Under 37 C.F.R. 1.290, mailed on Apr. 10, 2014, in corresponding U.S. Appl. No. 14/063,665; 9 pages.

(Continued)

*Primary Examiner* — Joseph Stoklosa
(74) *Attorney, Agent, or Firm* — Barbara A. Wrigley; Oppenheimer Wolff & Donnelly LLP

(57) ABSTRACT

An MRI compatible cable construct is provided. The cable is adapted to be used with a medical device in direct electrical contact with a patient. Each cable or cable set includes a plurality of filter components. The filter component comprises at least two filter components. One filter component may be a resonant filter at a distal end that resolves the issue of insufficient attenuation by effectively blocking the RF induced current on the cable from exiting the cable at the distal. The second filter component may comprise one or more non-resonant filter(s) or inductors positioned along the length of the cable that resolve(s) the issue of excessive heating of the resonant LC filter by significantly attenuating the current induced on the cable before it reaches the resonant LC filter.

31 Claims, 6 Drawing Sheets

(56) References Cited

U.S. PATENT DOCUMENTS

| | | | |
|---|---|---|---|
| 5,510,945 A | 4/1996 | Taylor et al. |
| 5,867,891 A | 2/1999 | Lampe |
| 5,951,539 A | 9/1999 | Nita et al. |
| 6,493,590 B1 | 12/2002 | Wessman et al. |
| 7,013,180 B2 | 3/2006 | Villaseca et al. |
| 7,174,219 B2 | 2/2007 | Wahlstrand et al. |
| 7,363,090 B2 | 4/2008 | Halperin et al. |
| 7,689,288 B2 * | 3/2010 | Stevenson et al. ............ 607/63 |
| 7,702,387 B2 | 4/2010 | Stevenson et al. |
| 7,751,903 B2 | 7/2010 | Stevenson et al. |
| 7,844,319 B2 | 11/2010 | Susil et al. |
| 7,844,343 B2 | 11/2010 | Wahlstrand et al. |
| 7,899,551 B2 | 3/2011 | Westlund et al. |
| 7,945,322 B2 | 5/2011 | Stevenson et al. |
| 7,983,764 B2 | 7/2011 | Bodner et al. |
| 8,145,324 B1 | 3/2012 | Stevenson et al. |
| 8,364,283 B2 | 1/2013 | Halperin et al. |
| 8,588,934 B2 | 11/2013 | Lloyd et al. |
| 8,588,938 B2 | 11/2013 | Lloyd et al. |
| 2002/0016589 A1 | 2/2002 | Swartz et al. |
| 2002/0095084 A1 | 7/2002 | Vrijheid et al. |
| 2003/0050557 A1 | 3/2003 | Susil et al. |
| 2003/0130738 A1 | 7/2003 | Hovda et al. |
| 2003/0135101 A1 | 7/2003 | Webler |
| 2003/0144721 A1 | 7/2003 | Villaseca et al. |
| 2004/0199069 A1 | 10/2004 | Connelly et al. |
| 2005/0222659 A1 | 10/2005 | Olsen et al. |
| 2005/0228452 A1 | 10/2005 | Mourlas et al. |
| 2006/0247684 A1 | 11/2006 | Halperin et al. |
| 2007/0018535 A1 | 1/2007 | Guedon et al. |
| 2007/0112398 A1 | 5/2007 | Stevenson et al. |
| 2007/0197890 A1 | 8/2007 | Boock et al. |
| 2007/0288058 A1 | 12/2007 | Halperin et al. |
| 2008/0024912 A1 | 1/2008 | Mallary et al. |
| 2008/0049376 A1 | 2/2008 | Stevenson et al. |
| 2008/0071313 A1 | 3/2008 | Stevenson et al. |
| 2008/0116997 A1 | 5/2008 | Dabney et al. |
| 2008/0119919 A1 | 5/2008 | Atalar et al. |
| 2008/0132985 A1 | 6/2008 | Wedan et al. |
| 2008/0132987 A1 | 6/2008 | Westlund et al. |
| 2008/0186123 A1 | 8/2008 | Wei et al. |
| 2008/0243218 A1 | 10/2008 | Bottomley et al. |
| 2008/0262584 A1 | 10/2008 | Bottomley et al. |
| 2009/0171421 A1 | 7/2009 | Atalar et al. |
| 2009/0243756 A1 | 10/2009 | Stevenson et al. |
| 2010/0016936 A1 | 1/2010 | Stevenson et al. |
| 2010/0100164 A1 | 4/2010 | Johnson et al. |
| 2010/0114276 A1 | 5/2010 | Min et al. |
| 2010/0160997 A1 | 6/2010 | Johnson et al. |
| 2010/0191236 A1 | 7/2010 | Johnson et al. |
| 2011/0046707 A1 | 2/2011 | Lloyd et al. |
| 2012/0071956 A1 | 3/2012 | Stevenson et al. |

OTHER PUBLICATIONS

International Search Report and Written Opinion, from corresponding application (PCT/US10/26232), U.S. Receiving Office, dated Apr. 30, 2010, 11 pages.

International Search Report and Written Opinion, from corresponding application (PCT/US13/44685), U.S. Receiving Office, dated Sep. 10, 2013, 10 pages.

Ozenbaugh, Richard Lee, et al., "Network Analysis of Passive LC Structures, " EMI Filter Design, Third Edition: 2011, pp. 18-1 to 18-11. CRC Press.

Whitaker, Jerry C., "Filter Devices and Circuits," The Resource Handbook of Electronics; 2001, 11 pages, CRC Press LLC, USA.

Extended European Search Report, from corresponding U.S. Appl. No. EP 10749339.7, European Patent Office, dated Dec. 5, 2013, 11 pages.

Third Party Submission under 37 C.F.R. 1.290, filed on corresponding U.S. Appl. No. 13/836,287; dated Jan. 22, 2014, 5 pages.

* cited by examiner

MRI COMPATIBLE CABLE

RELATED APPLICATION DATA

This application is a non-provisional of U.S. application Ser. No. 61/660,085, filed on Jun. 15, 2012, and is a continuation-in-part to U.S. application Ser. No. 12/743,954, filed May 20, 2010, which claims priority to International application Serial No.: PCT/US2010/026232, filed on Mar. 4, 2010, which also claims priority U.S. provisional application Ser. No. 61/157,482, filed on Mar. 4, 2009, the entireties of which are incorporated herein by reference.

BACKGROUND OF THE INVENTION

1. Field of the Invention

The invention relates to medical devices used in the magnetic resonance imaging (MRI) environment and in particular to a conductive cable that may be used to connect medical devices and other peripheral equipment to a patient.

2. Background of the Related Art

MRI has achieved prominence as a diagnostic imaging modality, and increasingly as an interventional imaging modality. The primary benefits of MRI over other imaging modalities, such as X-ray, include superior soft tissue imaging and avoiding patient exposure to ionizing radiation produced by X-rays. MRI's superior soft tissue imaging capabilities have offered great clinical benefit with respect to diagnostic imaging. Similarly, interventional procedures, which have traditionally used X-ray imaging for guidance, stand to benefit greatly from MRI's soft tissue imaging capabilities. In addition, the significant patient exposure to ionizing radiation associated with traditional X-ray guided interventional procedures is eliminated with MRI guidance.

MRI uses three fields to image patient anatomy: a large static magnetic field, a time-varying magnetic gradient field, and a radiofrequency (RF) electromagnetic field. The static magnetic field and time-varying magnetic gradient field work in concert to establish proton alignment with the static magnetic field and also spatially dependent proton spin frequencies (resonant frequencies) within the patient. The RF field, applied at the resonance frequencies, disturbs the initial alignment, such that when the protons relax back to their initial alignment, the RF emitted from the relaxation event may be detected and processed to create an image.

Each of the three fields associated with MRI presents safety risks to patients when a medical device is in close proximity to or in contact either externally or internally with patient tissue. One important safety risk is the heating that can result from an interaction between the RF field of the MRI scanner and the medical device (RF-induced heating), especially medical devices which have elongated conductive structures with tissue contacting electrodes, such as cables in pacemaker and implantable cardioverter defibrillator (ICD) leads, guidecables, and catheters. Thus, as more patients are fitted with implantable medical devices, and as use of MRI diagnostic imaging continues to be prevalent and grow, the need for safe devices in the MRI environment increases.

Exemplary interventional procedures include, for example, cardiac electrophysiology procedures including diagnostic procedures for diagnosing arrhythmias and ablation procedures such as atrial fibrillation ablation, ventricular tachycardia ablation, atrial flutter ablation, Wolfe Parkinson White Syndrome ablation, AV node ablation, SVT ablations and the like.

The foregoing procedures, among others, may require peripheral equipment such as electrophysiology recording systems, catheter tracking systems, external stimulators, surface electrocardiograms, 12-lead electrocardiograms, ablation generators, external defibrillators, pulse oximeters, various vital monitors and other devices and equipment in direct electrical contact with the patient. Conductive cables are used to connect these medical devices and peripheral equipment to the patient. In particular cables are used that operably connect medical devices and peripheral equipment to a patient's skin via a surface pad or patch. However, the RF-induced heating safety risk associated with cables in the MRI environment results from a coupling between the RF field and the cable. In this case several heating related conditions exist. One condition exists because the cable may electrically contact a patch adhesively or non-adhesively connected to tissue or skin. RF currents induced in the cable may be delivered through the cable into the tissue or skin, resulting in a high current density in the skin or tissue below the skin and associated Joule or Ohmic heating. Also, RF induced currents in the cable may result in increased local exposure to RF energy in nearby skin or other tissue, thus increasing the tissue's temperature. The foregoing phenomenon may be experienced as dielectric heating. Dielectric heating may occur even if the cable does not electrically contact tissue, for example if the cable was insulated from tissue. In addition, RF induced currents in the cable may cause Ohmic heating in the cable, itself, and the resultant heat may transfer to the patient. In such cases, it is important to attempt to both reduce the RF induced current present in the cable and to limit the current delivered into the surrounding skin and/or tissue.

Methods and devices for attempting to solve the foregoing problem are known. For example, high impedance cables limit the flow of current and reduce RF induced current; a resonant LC filter placed at the cable/patient interface may reduce the current delivered into the body through the cable, non-resonant components placed at the cable/patient interface may also reduce the current transmitted into the body; and co-radial cable sets may be used to provide a distributed reactance along the length of the cable thus increasing the impedance of the cable and reducing the amount of induced current.

Notwithstanding the foregoing attempts to reduce RF-induced heating, significant issues remain. For example, high impedance cables limit the functionality of the cable and do not allow for effective ablation, pacing or sensing. Resonant LC filters placed at the cable/patient interface inherently result in large current intensities within the resonant components resulting in heating of the filter itself, at times exceeding 200° C. Additionally, a resonant LC filter at the cable/patient interface can result in a strong reflection of the current induced on the cable and may result in a standing wave that increases the temperature rise of the cable itself and/or results in increased dielectric heating near the cable which in turn heats surrounding tissue to potentially unacceptable levels and may melt the catheter or lead body in which it is housed. Non-resonant components alone do not provide sufficient attenuation to reduce the induced current to safe levels. Additionally, the components will experience a temperature rise, if the conductor cross-sectional area is too small. While a cable with distributed reactance (i.e. coiled cables) can reduce the level of induced current on the cable, it does not sufficiently block the current that is induced on the cable from exiting the cable through points of electrical contact with skin or tissue. Thus, while coiled cables may work for certain short lengths or distances, in situations requiring longer lengths or distances, coiled cables do not by themselves provide enough impedance to block current.

Current technologies for reducing RF-induced heating in medical devices, especially those in which a conductive cable is used to connect a medical device and/or peripheral equipment to a patient, are inadequate. Therefore, new cable constructs are necessary to overcome the problems of insufficient attenuation of RF energy.

BRIEF SUMMARY OF THE INVENTION

It is an object of the invention to provide an improved method for reducing RF-induced heating of tissue by attenuating the RF current induced in a cable by MRI in situations where the cable connects peripheral equipment or devices to a patient's skin.

It is a further object of the invention to provide a novel cable construction that is MRI compatible and resolves the limitations of the current technology such as insufficient attenuation of RF energy.

It is a further object of the invention to provide a novel cable construction that maintains physical flexibility, maneuverability and the ability to bend.

In one embodiment the invention is a cable adapted to be used with a medical device in direct electrical contact with a patient. Each cable or cable set includes a plurality of filter components constructed from a single wire.

In one embodiment the filter component comprises two filter components. One filter component may be a resonant filter at or near the cable/patient interface that resolves the issue of insufficient attenuation by effectively blocking the RF induced current on the cable from exiting the cable at the cable/patient interface. The second filter component may comprise one or more non-resonant filter(s) or inductors positioned along the length of the cable that resolve(s) the issue of excessive heating of the resonant LC filter by significantly attenuating the current induced on the cable before it reaches the resonant LC filter. The non-resonant filters(s) may also attenuate the RF current reflected from the resonant LC filter thereby resolving the issue of the strong reflected power from the resonant filter and the associated dielectric heating.

In one embodiment, the non-resonant filters may comprise a plurality of multiple inductors placed in close proximity such as within approximately 1 cm or less for the purpose of providing more attenuation than a single filter alone, while still allowing the cable to bend.

In one embodiment, multiple non-resonant filters placed in close proximity may be formed to create a distributed reactance. For example, two co-radially wound wires may create a distributed reactance. In an alternative embodiment three or more co-radially wound wires may create a distributed reactance. A further alternative embodiment may include the use of two or more coaxially wound wires.

In one embodiment, the novel cable construct may include a single wire circuit therewithin thereby eliminating the need for bonding points which reduces the possibility of mechanical failure of the wire circuit.

In one embodiment the wires within the cable have a cross sectional area such that the resistivity of the cable at the MR operating frequency, 64 MHz for a 1.5 T MRI for example, is low enough to ensure that heating of the cable is minimal.

In one embodiment the cable may be used to connect peripheral equipment to the skin of a patient via a surface pad or patch.

In one embodiment the cable may be used to connect external catheter tracking systems to the skin of a patient.

In one embodiment the novel cable construct includes an elongated body housing a circuit, the elongate body having first and second ends. The elongate body defines a lumen therewithin which receives first and second circuits. First and second circuits each include a wire that forms a plurality of filters distributed along a length thereof. A clip may be located at the distal end of the elongate body that operably couples the cable to the skin of a patient. The second end of the elongate body is operably coupled to electronic controls of peripheral equipment or other medical devices. One filter formed by each wire within the cable construct may be a resonant LC filter at or near the cable/patient interface that resolves the issue of insufficient attenuation by effectively blocking the RF induced current on the cable from exiting the cable at the cable/patient interface. A second filter formed by each wire within the cable construct may comprise one or more non-resonant filter(s) or inductors positioned along the length of the elongate body that resolve(s) the issue of excessive heating of the resonant LC filter by attenuating the current induced on the wire before it reaches the resonant LC filter. The non-resonant filter(s) may also attenuate the RF current reflected from the resonant LC filter thereby resolving the issue of the strong reflected power from the resonant filter and the associated dielectric heating.

In another embodiment a cable construct includes an elongate body having first (distal) and second (proximal) ends. The first end or termination point of the cable is operably coupled to the skin of a patient in a manner known to those of skill in the art. The elongate body further defines a lumen therewithin which receives a plurality of wire circuits. Each individual wire comprising the plurality of circuits forms a plurality of non-resonant filters, or inductors, distributed along a length thereof. The second end of the elongate body may be operably coupled to electronic controls of peripheral equipment or other medical devices such as electrophysiology recording systems, catheter tracking systems, external stimulators, surface electrocardiograms, 12-lead electrocardiograms, ablation generators, external defibrillators, pulse oximeters, various vital monitors and other devices and equipment in direct electrical contact with the patient. Each individual wire comprising the plurality of circuits also forms a resonant LC filter positioned within the lumen of the elongate body at a distal end thereof at or near the cable/patient interface.

In another embodiment a cable construct includes an elongate body having a proximal end and a distal end, the elongate body defining a lumen therewithin. The distal end is operably coupled to a patient and the proximal end is operably coupled to electronic controls of peripheral equipment or other medical devices. The circuit is housed within the elongate body and includes one or more wires that form at least one non-resonant filter and at least one resonant LC filter. The resonant LC filter is positioned at the distal end of the elongate body proximate the cable/patient. The circuit may be flexible or rigid.

The unique functionality of the cable construct is accomplished through a required combination of non-resonant and resonant filtering components that act in combination to substantially reduce the potential for current to be induced on the lead assembly and prevent any current that is induced on the lead assembly from exiting the assembly.

In various embodiments the MR compatible cable construct may be constructed from a single, continuous wire or multiple lengths of non-continuous wire with the resonant LC filter formed by winding the wire such that the inductance and capacitance formed by a section of the wire are configured in an electrically parallel manner. The inductance of the LC filter may result from multiple individual coils/inductors that are arranged in series electrically and stacked physically. The parallel capacitance of the assembly may result from either capacitance between multiple stacked coils, capacitance between winding of an individual coil, or both.

In one unique construction of the invention, stacking the coils results in a substantially uniformly distributed capacitance between each of the coils that is electrically parallel to the inductance of the coils. Forming the cable construct from a continuous length of wire or multiple lengths of non-continuous wire allows the following:

Creation of tightly wound and physically bonded filters with a well-controlled inductance.

Stacking of individual coils in a manner to ensure predictable/repeatable inductance, distributed capacitance, and resonant frequency.

Constructing the cable in a manner that provides physical stability to the entire structure.

Creation of individual and distributed impedances that do not vary with lead configuration (bending/trajectory).

Minimizing the physical size of the individual filtering components such that each component occupies the minimal possible physical distance along the cable, as well as a minimum cable diameter (distance from centerline axis of the cable) thereby minimizing the size of the overall structure.

Ability to generate well-controlled filtering impedances of up to 15 k Ohms or greater at a desired frequency in the resonant section of the cable, which is not achievable with discrete components.

Integration of the entire assembly into a single, physically robust structure.

In another aspect of the invention the non-resonant filters have a uniformly distributed inductance along the length of the cable construct. The creation of a well-controlled uniformly distributed inductance along the non-resonant portion of the structure is due to the spaced-apart, repetitious pattern of the non-resonant components along the non-resonant portion of the structure, which spaced apart relationship may be zero in the case where a single non-resonant filter occupies the length of the non-resonant portion of the structure.

While multiple embodiments, objects, feature and advantages are disclosed, still other embodiments of the invention will become apparent to those skilled in the art from the following detailed description taken together with the accompanying figures, the foregoing being illustrative and not restrictive.

DETAILED DESCRIPTION OF THE INVENTION

In describing the invention herein, reference is made to an exemplary cable construct in accordance with the invention. It is contemplated that the current MR compatible cable construct may be used to connect medical devices and peripheral equipment to a patient. As will be appreciated by those skilled in the art the present invention may be used with any medical device or other types of peripheral. Further the exemplary cable construct may be used external to the body and still be in contact with body tissue such as the skin. Also as used herein, a cable is any conductive structure that is in electrical contact with a patient at the cable/patient interface.

Figure 1:
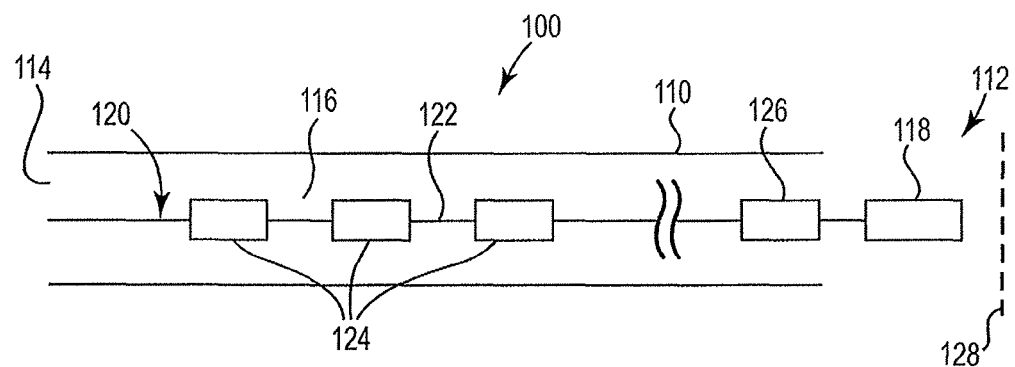
FIG. 1 is a block diagram depicting the basic components of the wire assembly housed within a cable.

FIG. 1 is a block diagram illustrating the cable construct 100 in its simplest form in accordance with the present invention. Cable 100 broadly includes elongate body 110 having first 112 and second 114 ends and defining a lumen 116 therewithin. Lumen 116 houses circuit 120. Circuit 120 includes at least one wire 122 forming a plurality of spaced apart filter components 124. Circuit 120 may be constructed from a single, continuous length of wire. Alternatively, the circuit 120 may be constructed with discrete filter components and a single wire or multiple lengths of non-continuous wire connecting the discrete filter components. Alternatively, the circuit 120 may be constructed with one wire forming filter components 124 and a discrete wire forming filter component 126. Any non-magnetic wire may be used in constructing the circuit in accordance with the present invention, including copper, titanium, titanium alloys, tungsten, gold and combinations of the foregoing. Optionally, wire 120 is a bondable wire such as heat, chemical or adhesively bondable to permit formation of the filters during manufacture with one wire. In the case in which multiple lengths of wire are used as connecting segments, the wires may be cast in silicone and/or heat-treated along the length at certain points to ensure that the wire does not shift within the cable. Alternatively, any wire that is sufficiently rigid so that it holds its shape when bent may be used. Wire 120 may also form filter component 126 positioned adjacent the cable/patient interface 128 to effectively block RF induced current from exiting the cable through the termination point 118. Additional filtering components 124 distributed along the length of the cable attenuate the induced current on the cable itself before the current reaches filter component 126 thereby avoiding excessive heating of filter component 126. Excessive heating will occur when the temperature of the filter rises approximately 2 to 4 degrees above the normal temperature of the tissue that the device contacts.

Preferably, filter component 126 at the cable/patient interface 128 is a resonant LC filter that resolves the problem of insufficient attenuation by effectively blocking the RF induced current on wire 122 and cable 100. Filter components 124 preferably include a plurality of non-resonant filters or inductors that address excessive heating of the resonant LC filter by significantly attenuating the current induced on the cable before the current reaches the resonant LC filter. Non-resonant filter components 124 may also attenuate the RF current reflected from resonant LC filter component 126 thereby attenuating the strong reflected power from the resonant LC filter 126 and reducing the associated dielectric heating.

Figure 2:
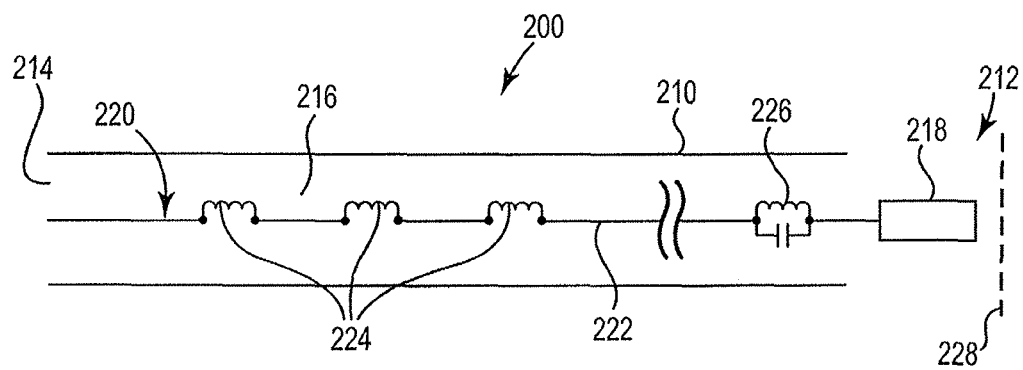
FIG. 2 is a diagram depicting an embodiment of the invention in which non-resonant filters are distributed along a cable in a spaced apart relationship with a resonant LC filter proximate the distal end.

FIG. 2 is a schematic diagram depicting an embodiment of the invention. Cable 200 broadly includes an elongate body 210 having first 212 and second 214 ends and includes lumen 216 therewithin. Lumen 216 houses circuit 220. Circuit 220 includes at least one conductive wire 222 forming a plurality of spaced apart filter components 224. Each circuit 220 may be constructed from a single, continuous length of non-magnetic wire such as copper, titanium, titanium alloys, tungsten, gold and combinations of the foregoing. Alternatively, each circuit may comprise multiple lengths of wire. As with the embodiment depicted in FIG. 1, wire 222 is a bondable cable such as heat, chemical or adhesively bondable to permit formation of the filters during manufacture with one wire. This eliminates the necessity for connection points at each end of each filter 224 and thereby improving the mechanical durability of the circuit 220 and reducing the manufacturing cost thereof. In the illustrated embodiment, the cable 200 includes resonant LC filter 226 positioned adjacent and proximal to the cable/patient interface 228. Resonant LC filter assembly 226 is adapted to effectively block RF induced current from exiting the cable 200 through the termination point 218. Resonant LC filter 226 effectively blocks RF induced current by being constructed such that the inductive and capacitive characteristics of the filter together resonate to create a high impedance at the MRI RF frequency of interest for example, approximately 64 MHz for a 1.5 Tesla MRI or approximately 128 MHz for a 3.0 Tesla MRI. Filtering components 224 distributed along the length of the cable attenuate the induced current on the cable itself before the current reaches resonant LC filter 226 thereby avoiding excessive heating of resonant LC filter 226. The filtering components 224 together preferentially create at least 1,000 or more Ohms of impedance along the entire circuit 220, for a lead length of approximately 1 meter. The electrical length of the electrode wire may be chosen to be a quarter wavelength or multiple thereof at the operating frequency of the MRI. Further, the electrical length of the electrode wire may be chosen to avoid standing waves and resonant conditions associated with electrical lengths of a half wavelength or multiple thereof at the operating frequency of the MRI. Those of skill in the art will appreciate that the amount of total impedance will necessarily change as the lead length varies. Each filtering component 224 may comprise an inductor formed by wire 222 with approximately 45 turns, creating approximately 150 Ohms, when sized to fit in an 8 French cable assuming an inside diameter of the inductor to be 0.045 inches. Fewer turns are necessary to create the same impedance for larger diameter inductors. Filtering components 224 may be spaced non-uniformly, such that the segments of cable between them each have a different resonant frequency, or substantially uniformly.

Figure 3A:
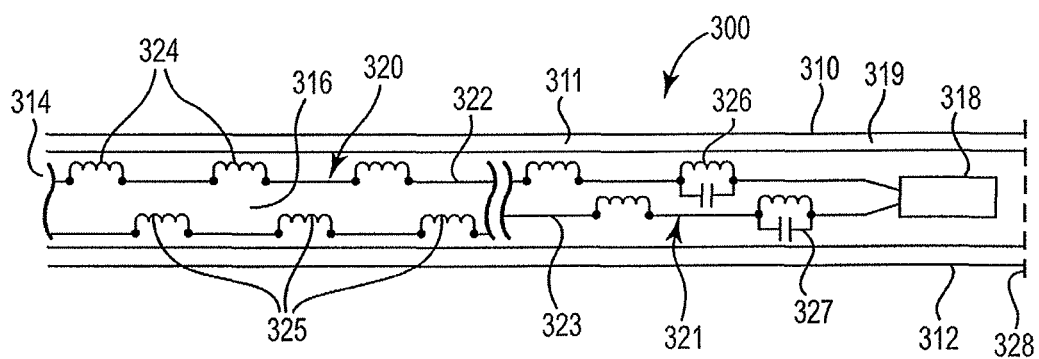
FIG. 3A is a sectional view of an exemplary cable including conductive electrode wires therewithin, each wire forming a resonant LC filter at the cable/patient interface and a plurality of non-resonant filters distributed within the cable.

Referring now to FIG. 3A a detailed sectional view of one embodiment of the invention is illustrated. Cable 300 includes elongate body 310 surrounded by jacket 311. Elongate body 310 includes first 312 and second 314 ends and includes lumen 316 therewithin. Second end 314 is adapted to be connected to medical devices and/or peripheral equipment, and may include a connector (not shown) known to those of skill in the art. Lumen 316 houses circuits 320, 321. Circuits 320, 321 each include one conductive wire 322, 323, respectively, located within the lumen 316 of cable 300. In an alternative embodiment, conductive wire 322, 323 can be embedded in jacket 311 of cable thereby decreasing the overall diameter of the lead assembly 300. Each conductive wire 322, 323 comprises a single length of conductive wire, each of which forms a plurality of spaced apart filter components 324, 325, respectively. Filter components 324, 325 comprise non-resonant filters or inductors that are spaced apart along the length of conductive wires 322, 323.

Figure 3B:
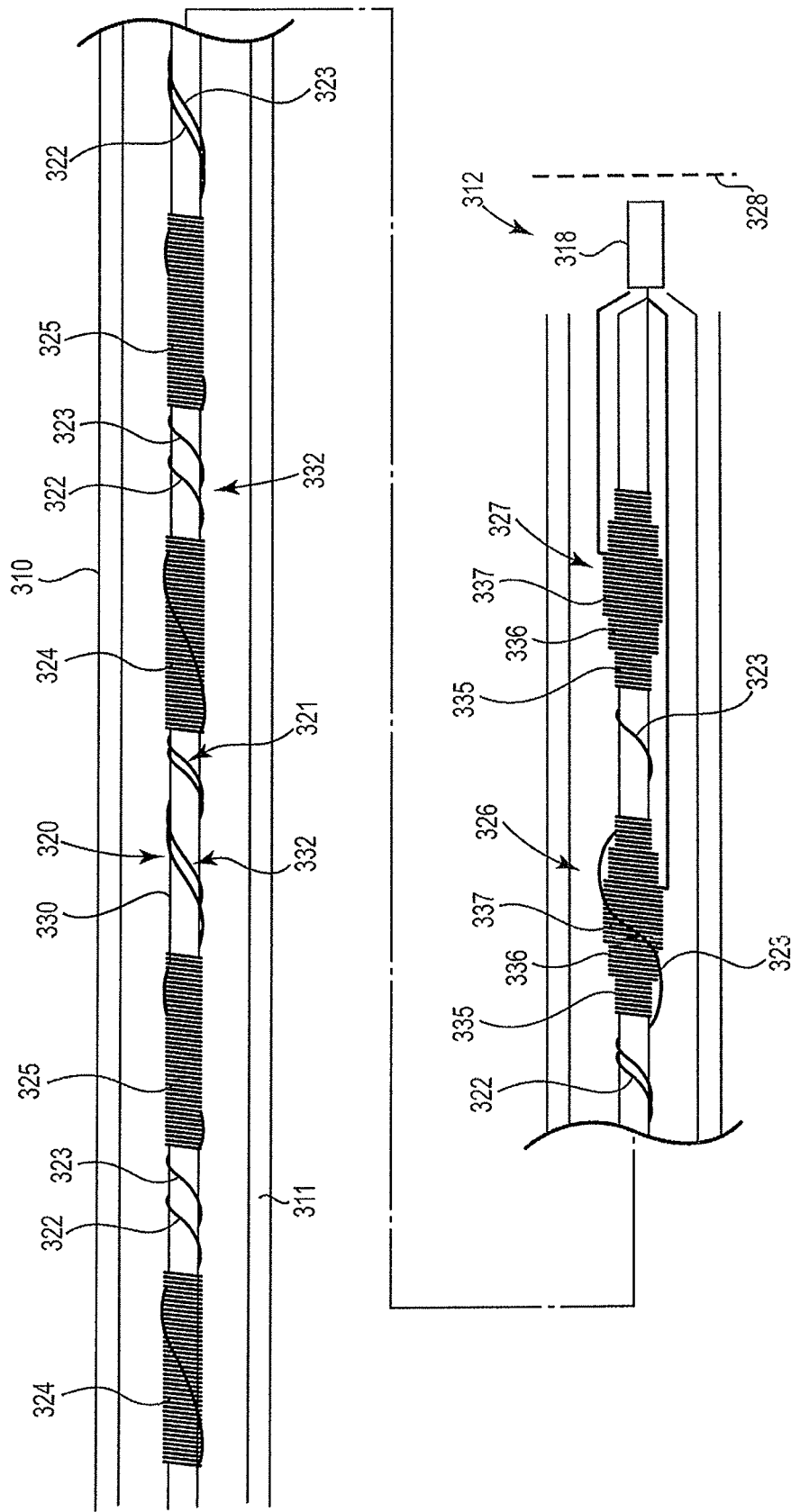
FIG. 3B shows a detailed view of the resonant LC filters and non-resonant filters of the novel cable construct.

The first and second conductive wires 322, 323 may be electrically insulated from one another. Both the first and second conductive wires 322, 323 may include an insulative or non-conductive coating. Preferably the insulative coating is a heat bondable material such as polyurethane, nylon, polyester, polyester-amide, polyester-imide, polyester-amide-imide and combinations of the foregoing. Alternatively, only one wire may be insulated. The wire insulation comprises the bondable material mentioned previously. In addition, circuits 320, 321, as best seen in FIG. 3B, are further electrically insulated as both wires 322, 323 are wound around non-conductive tube 330 defining a lumen therewithin. Tube 330 may be formed of a silicone material, Teflon, expanded tetrafluoroethylene (eTFE), polytetrafluoroethylene (pTFE), or the like, as described below. Winding the non-resonant filters 324, 325 or inductors around non-conductive tube 330 facilitates construction of the inductors and resonant LC circuit. Moreover, non-conductive tube 330 advantageously allows the circuits to maintain flexibility and maneuverability when placed inside elongate cable body 310.

Referring to FIG. 3A, lumen 316 houses circuits 320, 321 comprising wires 322, 323, respectively. Alternatively, wires 322, 323 may be embedded wholly or partially in cable jacket 311. As discussed previously, each wire 322, 323 forms a plurality of spaced apart filter components 324, 325 comprising non-resonant filters. As in previous embodiments, each circuit is optionally constructed from a single, continuous length of non-magnetic wire such as copper, titanium, titanium alloys, tungsten, gold and combinations of the foregoing; however, each circuit may alternatively be constructed from multiple lengths of wire or include discrete filter components connected by separate lengths of wires. If all filters are formed from one length of wire, it is important that the wire is a bondable cable such as heat, chemical or adhesively bondable to permit formation of the filters during manufacture with one cable as will be described below.

Referring now to FIG. 3B each circuit 320, 321 housed with cable 300 is constructed substantially similarly. Wires 322, 323 are wound over flexible tube 330 which is preferably made from polyimide, polyolefin, pTFE, eTFE, polyetherketone (PEEK) and other similar flexible materials. During manufacture a stiff rod (not shown) is placed inside of flexible tube 330 to provide added support for the assembly process. After manufacture, the rod is removed and the flexible tubing 330 with circuit constructs is placed in elongate cable body 310.

Each circuit 320, 321 is constructed separately with the first circuit 320 being constructed from the distal end to the proximal end starting with the most proximal resonant LC filter 326. Thus, assuming a plurality of circuits, the wire associated with the next most distal resonant LC filter 327 passes over the resonant LC filter that is most proximal. Passing a wire below a resonant LC filter will adversely affect its resonance. On the other hand, passing a wire underneath a non-resonant inductor will not adversely affect its performance. Thus, exemplary resonant LC filter 326 is constructed by layering of the wire 322 to form three layers 335, 336, 337. The ratio of turns from inner layer to outer layer may be approximately 3:2:1 resulting in a constant physical geometry of the resonant LC filter. Creating a resonant LC filter is apparent to those skilled in the art, and many embodiments would satisfy the requirements of this invention. For example, a capacitor may be placed in parallel with an inductor. Other types of resonant LC filters would also fall within the scope of the invention.

In the exemplary embodiment of FIGS. 3A and 3B, multiple layers of coiled cable are constructed such that the capacitance between the layers and individual turns provide the ratio of inductance to capacitance required to satisfy the resonant condition and provide the maximum impedance at the resonant frequency. As described previously, three layers may be used, the ratio of turns from inner layer to outer layer being approximately 3:2:1. This ratio results in high structural integrity, manufacturability, and repeatability. In the exemplary embodiment, wherein the resonant frequency of the resonant LC filter is approximately 64 MHz to block the RF from a 1.5 Tesla MRI, the inner layer may include 30 turns, the middle layer may include 20 turns, and the outer layer may include 10 turns. In general, the exact number of turns is determined by the space available and the desired resonant frequency. The impedance, bandwidth and quality factor of the resonant LC filter can be adjusted by modifying the ratio of the capacitance to the inductance of the filter. This may be accomplished by changing the number of turns, the number of layers, the ratio of turns between layers, or all of these. For example, the ratio may vary in each case by one, two or three turns to obtain the desired characteristics of the filter.

After forming the most proximal resonant LC filter 326, first wire 322 is helically wound around tube 330. Those of skill in the art will appreciate that connecting segments 332 do not necessarily need to comprise a specific numbers of turns around tube 330. Rather, it is important to wind the wires in such a manner as to include some slack or "play" thereby allowing the lead assembly to maintain its flexibility during use. Inductors 324 are next formed by coiling wire 322 over flexible tube 330. Each inductor 324 may be formed by helically winding or coiling wire 322 approximately forty-five turns, creating approximately 150 ohms, when sized to fit in an 8 French catheter assuming an inside diameter of the inductor to be 0.045 inches. Those of skill in the art will appreciate, however, that fewer turns may be necessary to create the same impedance for larger diameter inductors. Inductors 324 may be spaced non-uniformly, such that the segments of wire between them each have a different resonant frequency, or may be placed substantially uniformly.

Second circuit 321 is constructed next and substantially similarly to circuit 320. Those of skill in the art will appreciate that the exemplary cable construct illustrated in FIGS. 3A and 3B comprises two circuits 320, 321. However, any number of circuits can be constructed and in a preferred embodiment, depicted in FIG. 2, one circuit is used. In cables that use multiple circuits, however, the circuit that includes the most proximal resonant LC filter is constructed first and the circuit that includes the most distal resonant LC filter is constructed last so that the plurality of resulting cables housed within a catheter have the connecting wire segments passing over all proximal resonant LC filters. For example, constructing circuits 320, 321 may be done by starting at the proximal end first (rather than the distal end) so long as the circuit that includes the most proximal resonant LC filter is constructed first. In this way the connecting cable segments of the subsequently constructed circuits will always pass over all adjacent, proximal resonant LC filters so that resonance is not disturbed. Other assembly techniques will be apparent to those of skill in the art.

Figure 4:
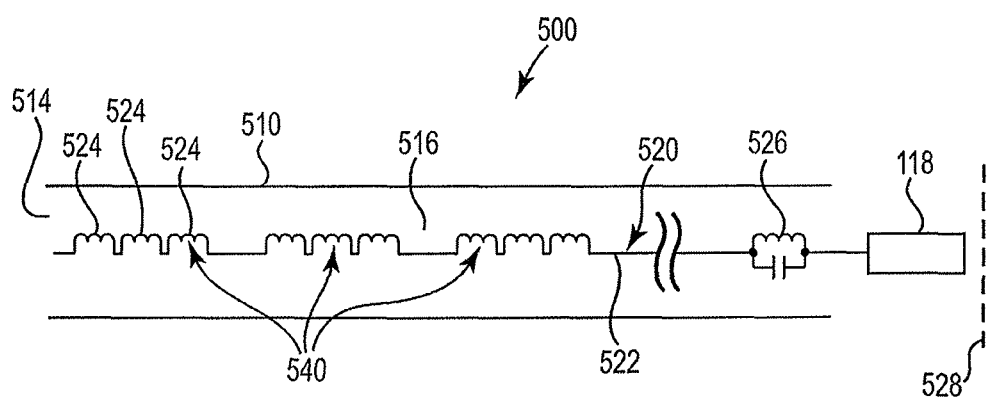
FIG. 4 depicts an embodiment of the invention in which multiple non-resonant inductors formed from a single wire are grouped together and distributed along the cable and further forming a resonant LC filter proximate the cable/patient interface.

Referring now to FIG. 4 one embodiment of the cable construct 500 in accordance with the invention is shown. Circuit 520 includes multiple, small non-resonant filters 524 that are grouped together to form a plurality of inductors 540 positioned in a spaced apart relationship along the length of conductive cable 522. This grouping of filters collectively increases the impedance of each non-resonant filter and reduces the current along the conductive circuit 522. As in other embodiments filter component at the termination point 518 located adjacent the cable/patient interface 528 includes resonant LC filter 526 that is adapted to effectively block RF induced current from exiting the cable 500 through the termination point 518. Groups 540 of non-resonant filters 524 distributed along the length of circuit 522 attenuate the induced current on the cable itself before the current reaches resonant LC filter 526 thereby avoiding excessive heating of resonant LC filter 526. Groups 540 of non-resonant filters 524 may also attenuate the RF current reflected from resonant LC filter 526 thereby attenuating the strong reflected power from the resonant LC filter 526. The embodiment depicted in FIG. 4 is constructed in much the same way as previously described.

Figure 5A:
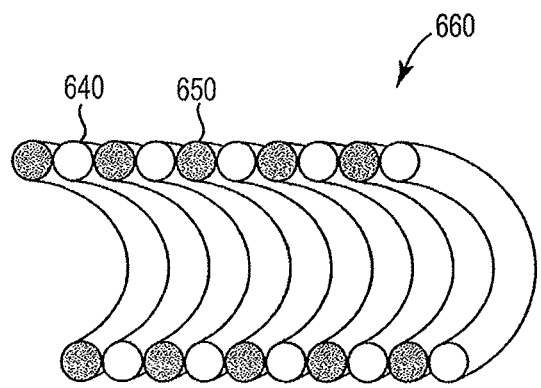
FIG. 5A is a perspective view depicting two co-radially wound wires forming a cable set.
Figure 5B:
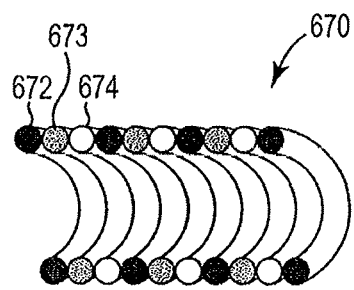
FIG. 5B is a perspective view depicting three co-radially wound wires forming a cable set.
Figure 5C:
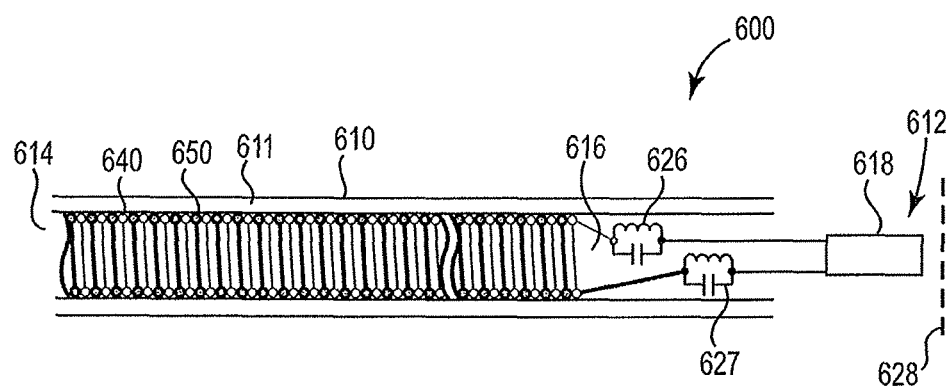
FIG. 5C is a schematic view of the co-radially wound wires of FIG. 5A with resonant LC filters adjacent the cable/patient interface.

Referring now to FIGS. 5A-FIG. 5C an alternative embodiment 600 of the cable construct in accordance with the invention is shown. As can be seen in FIG. 5A two wires 640, 650 are provided and wound in a co-radial fashion. The co-radially wound wires 640, 650 share a common magnetic flux channel in the center of the windings, such that common mode RF present on the cable will tend to cancel and thus be attenuated. As seen in FIG. 5B, three wires 672, 673, 674 are provided and wound in a co-radial fashion. The co-radially wound wires 672, 673, 674 share a common magnetic flux channel in the center of the windings, such that common mode RF present on the cable will tend to cancel and thus be attenuated. This co-radial approach may comprise any number of co-radially wound wires. Those of skill in the art will appreciate that co-radially wound wires behave as non-resonant filters.

Referring to FIG. 5C, the cable construct of FIG. 5A is shown in detail, cable 600 includes elongate body 610 surrounded by jacket 611. Elongate body 610 includes first 612 and second 614 ends and includes lumen 616 therewithin. Second end 614 is adapted to be connected to medical devices and peripheral equipment external to the patient body, and may include a connector (not shown). Lumen 616 houses co-radially wound conductive wires 640, 650. Each co-radially wound wire 640, 650 is wound in the same direction and the coils have the same diameter. When the cable is exposed to an RF field, as during an MRI scan, the co-radially wound cables 640, 650 tend to block higher frequency common mode RF current from being transmitted along the length of a cable. Each co-radially wound conductive wire 640, 650 may have an equal or unequal number of turns. Preferably, however, the conductive wires 640, 650 include an equal number of turns to minimize the amount of RF leakage from the coil, such leakage resulting in less effective RF current blocking. In the embodiment shown in FIG. 5C, the co-radially wound wires 640, 650 extend substantially along the entire length of the cable, proximal to the resonant LC filter assembly.

In the exemplary coiled configuration, first and second conductive cables are electrically insulated from one another. Both the first and second wires 640, 650 may include an insulative or non-conductive coating. The insulative coating may be formed of a polyurethane material, nylon, polyester, polyester-amide, polyester-imide, polyester-amide-imide, silicone material, Teflon, expanded tetrafluoroethylene (eTFE), Polytetrafluoroethylene (pTFE), and the like. Alternatively, only one wire may be insulated. In any case, the wires should be electrically isolated from each other.

As in previous embodiments, each co-radially wound wires 640, 650 is constructed from a single, continuous length of non-magnetic wire such as copper, titanium, titanium alloys, tungsten, gold and combinations of the foregoing. If each circuit in the cable is constructed from one length of wire, it may be a bondable wire such as heat, chemical or adhesively bondable to permit formation of the filters during manufacture of the cable. Alternatively, several lengths of non-continuous wire may be used and still fall within the intended scope of the invention. In such case the wires may be cast in silicone and heat-treated in certain location to ensure that the wire does not shift within the cable. Alternatively, glue or a circuit having sufficient rigidity so that it holds its shape when bent may be used to prevent compromise of the circuit from shifting.

As best seen in FIG. 5C first and second resonant LC filter assemblies 626, 627 are constructed as hereinbefore described. Resonant LC filters 626, 627 may be placed adjacent and proximal to the cable/patient interface to effectively block RF induced current from exiting the cable through the termination point 618. Co-radially wound wires 640, 650 act like non-resonant filters and attenuate the induced current on the cable itself before the current reaches the resonant LC filter thereby avoiding excessive heating.

As with other embodiments, wires 640, 650 are co-radially wound over a length of flexible tubing 340 made from polyimide, polyolefin, pTFE, eTFE, polyetherketone (PEK) and other similar flexible materials. The choice between utilizing cables with co-radially wound wires versus discrete inductors on each cable depends on several factors. Co-radially wound cables can be implemented with a smaller diameter, since one wire never needs to pass over or under another, except at the resonant LC filters. However, the impedance of the discrete inductor approach may be more predictable and is not as dependent on length or bend of the device.

In the various embodiments presented herein the conductor includes a sufficient cross-sectional area such that the resistivity of the conductor at the MR operating frequency of 64 MHz for a 1.5 Tesla MRI is low enough to ensure that at Joule heating of the cable is minimal. In one embodiment, the cable may be a 36 AWG copper magnet cable for a circuit that is approximately one meter in length. Numerical modeling such as for example Finite Difference Time Domain (FDTD) or Method of Moments may be used to approximate the expected current for a particular device. The length of cable being used and the expected trajectory in the patient determines the desired total impedance across the circuit. Thus, for any particular length of cable the appropriate gauge may then be selected.

A current of 100 mA DC will result in approximately a 10° rise in temperature in a short section of coiled 40 AWG cable. For a 36 AWG cable, the temperature rise is reduced to a 2° rise in temperature. For AC, the conductor resistance increases with frequency. An increase of five-fold or greater is possible when comparing the DC resistance to the resistance of 64 MHz, which directly translates to a greater temperature rise of the conductor for the same power input. The novel cable construct in accordance with the present invention is configured to be integrated into a 10 French or smaller cable.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed:

1. A cable construct comprising: an elongate body having a proximal end and a distal end, said elongate body defining a lumen therewithin, the distal end arranged and configured to be operably coupled to a patient and the proximal end operably coupled to a medical device or peripheral equipment; and at least one circuit housed within said elongate body and comprising one or more wires, said one or more wires forming at least one non-resonant filter and at least one resonant LC filter, said resonant LC filter positioned proximate the distal end of said elongate body.

2. The cable construct of claim 1 wherein said at least one resonant LC filter is a resonant parallel LC filter.

3. The cable construct of claim 1 further comprising at least one electrode.

4. The cable construct of claim 1 wherein said at least one non-resonant filter comprises a plurality of non-resonant filters.

5. The cable construct of claim 1 wherein said at least one non-resonant filter is constructed from a length of wire that is continuous or not continuous with a length of wire used to construct said at least one resonant LC filter.

6. The cable construct of claim 1 wherein said one or more wires comprise multiple lengths of non-continuous wire.

7. The cable construct of claim 3 wherein said plurality of non-resonant filters are positioned in a spaced apart relationship along a length of said electrical circuit.

8. The cable construct of claim 3 wherein said at least one electrical circuit comprises a plurality of circuits and said at least one electrode comprises a plurality of electrodes wherein each one of said plurality of circuits is electrically coupled to a separate electrode.

9. The cable construct of claim 1 wherein said one or more wires comprise a circuit board trace.

10. The cable construct of claim 1 wherein said one or more wires comprise a conductive lumen.

11. The cable construct of claim 1 wherein said one or more wires are selected from the group consisting of copper, titanium, titanium alloys, tungsten, gold and combinations of the foregoing.

12. The cable construct of claim 1 wherein one or more wires include an insulative coating bondable by heat, chemical or adhesive means.

13. The cable construct of claim 1 wherein said at least one resonant LC filter is configured to effectively block RF induced current from exiting said cable construct.

14. The cable construct of claim 1 wherein said at least one non-resonant filter is configured to attenuate induced current on said one or more wires before a current passing therethrough reaches said at least one resonant LC filter thereby avoiding excessive heating of said at least one resonant LC filter.

15. The cable construct of claim 1 wherein said at least one resonant LC filter is constructed such that the inductive and capacitive characteristics resonate to create a maximal impedance at approximately 64 MHz for a 1.5 Tesla MRI.

16. The cable construct of claim 1 wherein said at least one resonant LC filter is constructed such that the inductive and capacitive characteristics resonate to create a maximal impedance at approximately 128 MHz for a 3.0 Tesla MRI.

17. The cable construct of claim 1 wherein said at least one non-resonant filter is formed with approximately 45 turns of said electrode wire.

18. The cable construct of claim 3 wherein said one or more non-resonant filters are positioned along the length of the body in a spaced apart relationship, said spaced apart relationship comprising uniform or non-uniform spacing.

19. The cable construct of claim 3 wherein said at least one electrode comprises a ring electrodes.

20. The cable construct of claim 3 wherein said at least one electrode comprises at least one tip electrode.

21. The cable construct of claim 3 wherein said at least one electrode comprises a plurality of electrodes positioned in a parallel relationship on either side of said elongate body.

22. The cable construct of claim 12 wherein said insulative coating is selected from the group consisting of polyurethane, nylon, polyester, polyester-amide, polyester-imide, polyester-amide-imide and combinations of the foregoing.

23. The cable construct of claim 1 wherein said electrical circuit is housed entirely within the lumen of said elongate body.

24. The cable construct of claim 1 further comprising a flexible tube around which said at least one non-resonant and resonant LC filters are helically wound.

25. The cable construct of claim 1 wherein said at least one resonant LC filter comprises an inner layer, a middle layer and an outer layer formed from said electrode wire in a ratio of turns of approximately 3:2:1.

26. The cable construct of claim 1 wherein said at least one resonant LC filter comprises an inner layer of approximately 30 turns, a middle layer of approximately 20 turns, and an outer layer of approximately 10 turns of said electrode wire.

27. The cable construct of claim 4 wherein said plurality of non-resonant filters are configured to create at least 1,000 or more Ohms of impedance along said electrical circuit for each one meter of cable construct length.

28. The cable construct of claim 1 wherein the circuit is flexible.

29. The cable construct of claim 1 wherein the circuit is rigid.

30. The cable construct of claim 1 wherein the cable construct is MRI compatible.

31. The cable construct of claim 1 wherein said at least one non-resonant filter and said at least one resonant LC filter comprise discrete filters structured to be joined by multiple connecting segments of electrode wire.

* * * * *